United States Patent [19]

Haas et al.

[11] 4,188,396
[45] Feb. 12, 1980

[54] NEW PHENYLAZACYCLOALKANES

[75] Inventors: Georges Haas, Binningen; Alberto Rossi, Oberwil; Pier G. Ferrini, Binningen; Oswald Schier, Oberwil, all of Switzerland

[73] Assignee: Ciba-Geigy Corporation, Ardsley, N.Y.

[21] Appl. No.: 867,644

[22] Filed: Jan. 6, 1978

[30] Foreign Application Priority Data

Jan. 17, 1977 [CH] Switzerland .......................... 529/77

[51] Int. Cl.² ................ C07D 211/22; A61K 31/445; C07D 211/14
[52] U.S. Cl. .................................. 424/267; 546/192; 546/236
[58] Field of Search ...................... 260/293.72, 293.83; 424/267; 546/192, 236

[56] References Cited

U.S. PATENT DOCUMENTS

| 3,334,104 | 8/1967 | Houlihan | 260/293.72 |
| 3,458,521 | 7/1969 | Jack et al. | 260/293.72 |
| 3,801,581 | 4/1974 | Rossi | 260/293.72 |
| 4,024,151 | 5/1977 | Wade et al. | 260/295 AM |

FOREIGN PATENT DOCUMENTS 804204 8/1973 Belgium .

OTHER PUBLICATIONS

Protiva et al., "Collect. Czech. Chem. Comm.", (1975), vol. 40, No. 12, pp. 3904-3923.
Chem. Abstracts, (Abstracting Protiva et al. in "Collect. Czeck. Chem. Comm.", vol. 32, No. 8, pp. 2840-2853), vol. 67, Item 90643x (1967).

Primary Examiner—Alan L. Rotman
Assistant Examiner—Robert T. Bond
Attorney, Agent, or Firm—John J. Maitner

[57] ABSTRACT

New 4-(phenyl)-piperidine compounds of the general formula I

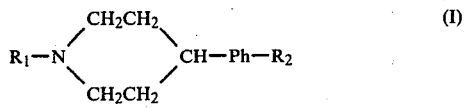

in which $R_1$ represents hydrogen or lower alkyl, Ph represents a p-phenylene group optionally substituted by lower alkyl, lower alkoxy, nitro and/or halogen, and $R_2$ represents lower alkyl, and pharmaceutically acceptable acid addition salts thereof are useful as antidepressant agents.

7 Claims, No Drawings

NEW PHENYLAZACYCLOALKANES

The invention relates to new aliphatically substituted 4-(phenyl)-1-aza-cycloalkanes, to processes for producing them, to pharmaceutical preparations containing these new compounds, and to the use thereof.

The invention relates in particular to 4-(phenyl)-piperidine compounds of the general formula I

wherein $R_1$ represents a radical of the formula

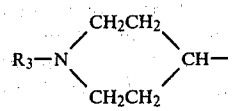

in which $R_3$ represents hydrogen or lower alkyl, Ph represents a p-phenylene group optionally substituted by lower alkyl, lower alkoxy, nitro and/or halogen, and $R_2$ represents lower alkyl, in the free form or in salt form.

By "lower" organic compounds and radicals derived from these are meant, in the foregoing and in the following, in particular those compounds and radicals containing up to 7 carbon atoms, especially up to 4.

Lower alkyl contains for example up to 7 carbon atoms, particularly up to b 4 carbon atoms, and can be branched-chain and can be bound in any position, but is preferably straightchain. Examples which may be mentioned are, in particular, butyl, propyl, isopropyl and especially ethyl and methyl.

Lower alkoxy contains, for example, up to 7 carbon atoms, particularly up to 4 carbon atoms, and can be branched-chain, and the oxy group can be bound in any position, but it is preferably straight-chain. Examples which may be mentioned are butoxy, propoxy, isopropoxy, ethoxy and, in particular, methoxy.

Halogen is for example halogen up to and including atomic number 35, especially chlorine.

The compounds of the general formula I and their pharmaceutically applicable salts possess valuable pharmacological properties. They thus have a pronounced reserpine-antagonistic action, which can be varied, for example, on the mouse on the basis of the reversal of hypothermia, produced by reserpine, after administration in doses of about 3 to about 100 mg/kg p.o., and on the rat in the palpebral fissure test on the basis of ptosis, produced by reserpine, with doses of about 10 to about 100, e.g. of about 3 to about 30, mg/kg p.o. The new compounds exhibit in particular a tetrabenazine-antagonistic action, which can be demonstrated for example on the rat, in the tetrabenazine catalepsy test, with does of about 3 to about 30 mg/kg i.p.

Furthermore, the new compounds have an inhbititory effect on the absorption of noradrenaline, as can be shown in the case of the absorption of noradrenaline in the brain of the rat, using doses of about 10 to 100 mg/kg p.o. In addition, they produce in doses of about 30 to about 300 mg/kg p.o an inhibition of mono-amino oxidase in the brain of the rat, which can be verified by means of serotonin or phenethylamines as substrate, and a 5-hydroxy-tryptamine potentiation, which can be shown on the mouse with doses of about 10 to 100 mg/kg p.o. The new compounds are moreover better tolerated than hitherto known compounds having the same direction of action and a similar structure.

The new compounds are accordingly useful as psychopharmacological agents, especially as antidepressants, for example for the treatment of mental depression.

The invention relates above all to compounds of the general formula I wherein $R_1$, $R_3$ and Ph have the given meanings, and $R_2$ represents straight-chain lower alkyl, in the free form or in the salt form.

The invention relates in particular to compounds of the general formula I wherein $R_1$ has the given meaning, Ph represents p-phenylene optionally monosubstituted by lower alkyl, especially that having up to 4 carbon atoms, such as methyl, lower alkoxy, particularly that having up to 4 carbon atoms, such as methoxy, or by halogen, especially halogen up to atomic number 35, such as chlorine, $R_2$ represents straight-chain lower alkyl having in each case up to 7, e.g. up to 4, carbon atoms, and $R_3$ represents hydrogen or lower alkyl having up to 4 carbon atoms, such as methyl, in the free form or in the salt form.

The invention relates especially to compounds of the general formula I wherein $R_1$ has the given meaning, Ph represents p-phenylene monosubstituted by lower alkyl having up to 4 carbon atoms, such as methyl, lower alkoxy having up to 4 carbon atoms, such as methoxy, or by halogen up to atomic number 17, such as chlorine, or in particular unsubstituted p-phenylene, $R_2$ represents lower alkyl having up to 4 carbon atoms, such as butyl, propyl, or especially ethyl or methyl, and $R_3$ represents hydrogen or lower alkyl having up to 4, e.g. up to 2, carbon atoms, such as methyl, in the free form or in the salt form.

The invention relates particularly to the compounds of the general formula I which are mentioned in the Examples, in the free form and in the salt form.

The new compounds can be produced by methods known per se.

A preferred procedure comprises cyclising a compound of the general formula

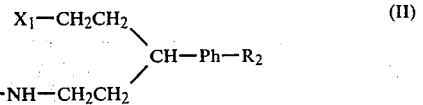

wherein $X_1$ represents an optionally reactive esterified hydroxyl group or an amino group of the formula $R_3$—NH—, or a salt thereof; and, optionally, converting the resulting compound into another compound of the general formula (I), separating an obtainable isomeric mixture (mixture of racemates) into the pure isomers (racemates), resolving an obtainable racemate into the optical antipodes, and/or converting an obtainable free compound into a salt, or an obtainable salt into the free compound or into another salt.

A reactive esterified hydroxyl group is for example a hydroxyl group esterified with a strong acid, e.g. with a mineral acid such as a hydrohalic acid, e.g. with hydriodic, hydrobromic or hydrochloric acid, or with an organic sulphonic acid, e.g. with benzene-, p-toluene-, p-bromobenzene-, methane- or ethanesulphonic acid.

The cyclisation occurring with the splitting-off of $HX_1$ can be effected in the usual manner, for example by warming or moderate heating, e.g. up to 200° C., dry or, if necessary, in the presence of an inert solvent, and/or in the presence of a condensation agent. Starting with compounds in which $X_1$ is reactive esterified hydroxyl, there is used, e.g., a basic condensation agent such as a tertiary amine, e.g. triethylamine or pyridine, or an organic base, e.g. a carbonate or hydroxide of alkali metals or alkaline-earth metals, such as potassium hydroxide. Starting with compounds in which $X_1$ is hydroxyl, the reaction is performed, e.g., in the presence of a waterbinding agent, e.g. dicyclohexylcarbodiimide, and/or with removal by distillation of the reaction water, e.g. by means of azeotropic distillation with benzene or toluene or with a xylene.

The starting materials of the formula (II) are known or can be produced by methods known per se, for example by reaction of a compound of the formula IIa

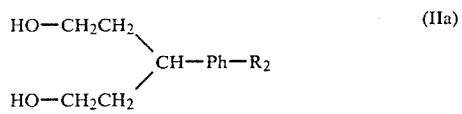

with a sulphonating or halogenating agent, such as with an organic sulphonic acid halide, with thionyl chloride or phosphorus tribromide, and subsequent reaction of the resulting compound of the formula IIb

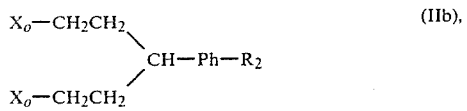

wherein at least one of the radicals $X_o$ represents a reactive esterified hydroxyl group, and the other optionally hydroxyl, with an amine of the formula $R_3$—$NH_2$, or with a salt thereof, in the usual manner.

The new compounds can also be produced by splitting off from a compound of the general formula III

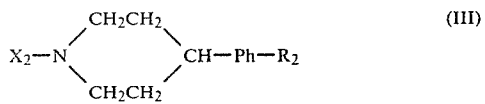

wherein $X_2$ represents a radical which can be split off, or from a salt thereof, the radical $X_2$, and, optionally, performing one or more of the aforementioned additional operations.

Such radicals $X_2$ which can be split off are, in particular, radicals which can be split off by solvolysis, especially by hydrolysis or by aminolysis or ammonolysis or by reduction.

Radicals which can be split off by solvolysis are, for example, acyl groups, such as acyl groups of organic acids, e.g. optionally halogenated lower alkanoyl groups, such as fluorinated lower alkanoyl groups, for example butyryl, propionyl, acetyl or trifluoroacetyl, or benzoyl groups, or optionally functionally modified carboxyl groups, e.g. esterified carboxyl groups, such as alkoxycarbonyl groups, e.g. the tert.-butoxycarbonyl group or the methoxycarbonyl group, aralkoxycarbonyl groups, such as phenyl-lower-alkoxycarbonyl groups, e.g. carbobenzoxy, also halogenocarbonyl groups, e.g. the chlorocarbonyl group, β-arylsulphonylethoxycarbonyl groups, such as β-toluenesulphonyl- or β-bromobenzenesulphonylethoxycarbonyl, or β-arylthioethyl groups or β-arylsulphonylethyl groups, such as β-(p-toluenesulphonyl)-ethyl groups or 2-(p-tolylthio)-ethyl groups, or cyano groups or silyl groups, such as the trimethylsilyl group.

Radicals which can be split off by reduction are, for example, α-arylalkyl groups such as benzyl groups, or α-aralkoxycarbonyl groups such as benzyloxycarbonyl groups, arylsulphonyl groups, e.g. p-toluenesulphonyl groups or 2-halogenoalkoxycarbonyl groups, such as the 2,2,2-trichloroethoxy-, 2-iodoethoxy- or 2,2,2-tribromoethoxycarbonyl groups.

Siolvolysis is performed in the usual manner, e.g. by hydrolysis in the presence of hydrolysing agents, or by reaction with ammonia or with a suitable amine. Thus, in the case of hydrolysis the reaction is performed, for example, in the presence of acid agents, such as an aqueous mineral acid such as sulphuric acid or hydrohalic acid, or in the presence of an organic acid, e.g. a suitable carboxylic acid, such as an α-halogenoalkanecarboxylic acid, for example trifluoro- or chloroacetic acid, an organic sulphonic acid, for example benzene- or toluenesulphonic acid, or in the presence of acid ion exchangers. or in the presence of basic agents, e.g. alkali hydroxides, such as sodium hydroxide, or in the presence of ammonia or amines, e.g. hydrazine, if necessary at elevated temperature.

Aminolysis or ammonolysis can be performed in the customary manner, for example by reduction with ammonia or with an amine, such as hydrazine or a mono- or dialkylamine or alkylene- or oxa-, aza- or thialkyleneamine, e.g. with ammonia, hydrazine, methyl- or dimethylamine, morpholine or piperidine, if necessary in an inert solvent and/or at elevated temperature.

Esterified carboxyl groups, arylsulphonyl groups and cyano groups can be split off in an advantageous manner by acid agents, such as by a hydrohalic acid. Particularly suitable in this respect is, e.g., splitting off by means of aqueous hydrochloric acid, optionally in admixture with acetic acid. It is also possible to solvolytically split off, e.g., a tert.-butoxycarbonyl group under anhydrous conditions by treatment with a suitable acid, such as with trifluoroacetic acid.

The reductive splitting-off of radicals $X_2$ which can be split off by reduction is effected in the usual manner, starting with α-arylalkyl groups such as benzyl groups, or α-aralkoxycarbonyl groups such as benzyloxycarbonyl groups, in particular by reaction with catalytically activated hydrogen, such as by hydrogen in the presence of a hydrogenating catalyst, e.g. optionally sulphidised palladium on charcoal, or Raney nickel, or starting with arylsulphonyl groups, e.g. p-toluenesulphonyl groups, or with 2-halogenoalkoxycarbonyl groups, such as the 2,2,2-trichloroethoxy-carbonyl group or the 2-iodoethoxy- or 2,2,2-tribromoethoxy-carbonyl group, especially by means of metallic reduction, e.g. with nascent hydrogen. Nascent hydrogen can be obtained, e.g., by reaction of metal or metal alloys, such as amalgams, with agents releasing hydrogen, such as carboxylic acids, alcohols or water, with in particular zinc or zinc alloys together with acetic acid being suitable. The hydrogenolysis of 2-halogenoalkoxycarbonyl groups can moreover be performed by means of chromium(II) compounds, such as chromium(II) chloride or chromium(II) acetate. The splitting-off of an arylsulphonyl group, such as the toluenesulphonyl group, by reduction with nascent hydrogen can however also be effected by means of an alkali metal, such as lithium or sodium, in liquid ammonia. In carrying out the reduction, care must be taken to ensure that other reducible groups are not attacked.

The starting materials of the general formula (III) are known or can be produced by methods known per se, for example by reacting a corresponding 1-$X_2$-4-phenyl-piperidine, optionally substituted in the phenyl moiety, in the presence of aluminium trichloride, with a lower alkanoyl halide; and reducing in the 1-$X_2$-4-(lower alkanoylphenyl)-piperidine thus obtainable the lower alkanoyl group in the customary manner, e.g. by reacting hydrogen in the presence of palladium charcoal, to lower alkyl. The 1-$X_2$-4-phenyl-piperidine compounds to be used for the purpose can be produced, e.g., by reacting a corresponding phenylmagnesium bromide with 1-benzyl-4-piperidone; subsequently hydrogenating in the presence of palladium charcoal; and introducing into the 4-phenyl-piperidine compound thus obtainable, by reaction with the corresponding halide, the radical $X_2$.

Compounds of the formula (III) wherein $X_2$ represents an α-aralkyl, β-arylthioethyl or silyl group can also be produced by reaction of the corresponding 4-(1-$X_2$)-piperidone with an optionally substituted p-$R_2$-phenylmagnesium bromide or p-$R_2$-phenyllithium in the usual manner, e.g. in ether or tetrahydrofuran, and subsequent reductive replacement, e.g. by catalytic hydrogenation, of the formed hydroxyl group with hydrogen; or by introduction of the radical $X_2$, e.g. of an arylalkyl group, into a 4-(p-$R_2$-phenyl)-δ-valerolactam, and subsequent reduction of the lactamic oxo group in the customary manner, e.g. with lithium aluminium hydride.

The new compounds can be produced also by reducing in a compound of the general formula IV

$$R_1'\text{—Ph—}R_2' \qquad (IV)$$

wherein $R_1'$ represents a radical $R_1$ and/or $R_2'$ a radical $R_2$, subject to the proviso that at least one of these radicals contains at least one double bond, or in a salt thereof, the double bond(s) of the radical $R_1'$ and/or of the radical $R_2'$, and, optionally, carrying out one or more of the aforementioned additional operations.

A radical $R_1'$ containing at least one double bond is for example a 4-pyridyl group optionally partially hydrogenated and optionally N-lower-alkylated.

A radical $R_2'$ having at least one double bond is for example an unsaturated aliphatic hydrocarbon radical, such as lower alkenyl, e.g. methallyl, isopropenyl, propen-2-yl, vinyl or allyl, or lower alkynyl such as ethynyl or propargyl.

If $R_1'$ represents a 4-pyridyl group, it can be advantageous to start with the corresponding, optionally N-lower-alkylated pyridinium compound.

The reduction is performed in the usual manner, e.g. with catalytically activated hydrogen, for example in the presence of Raney nickel or a noble metal catalyst such as platinum or palladium, optionally in the form of their oxides or on charcoal, advantageously in an inert solvent, e.g. in an alkanol, or dioxane, and optionally under pressure. It is also possible however to perform the reduction with nascent hydrogen, e.g. with sodium in ethanol. It is advisable to select in each case the conditions which will ensure that other groups in the molecule, e.g. the p-phenylene group, are not attacked.

N-Lower-alkyl-1,2,5,6-tetrahydropyridyl groups and N-loweralkylpyridinium groups $R_1'$ in compounds of the formula (IV) can also be reduced by reaction with a di-light-metal-hydride in the customary manner, e.g. with sodium borohydride, for example in a lower alkanol such as isopropanol, or with lithium aluminium hydride, for example in an aliphatic ether, such as in diethyl ether, dioxane or tetrahydrofuran.

The starting materials of the general formula (IV) are known and can be produced by methods known per se.

Compounds of the formula (IV) wherein $R_1'$ represents a 4-pyridyl group can be obtained for example by the usual reaction of a 4-metal-pyridine, e.g. of 4-lithium-pyridine, with a compound of the formula $R_2'$—Ph—Hal, wherein Hal is halogen, e.g. bromine or chlorine, and $R_2'$ represents an optionally unsaturated aliphatic hydrocarbon radical other than ethynyl. From the pyridyl compounds obtained, e.g., in this manner, it is then possible to produce, by customary quaternisation, e.g. with a lower alkyl halide, or by conversion into a salt, e.g. with a hydrohalic acid, the corresponding, optionally N-lower-alkylated pyridyl compounds.

Compounds of the formula (IV) wherein $R_1'$ represents an N-lower-alkylated 4-(1,2,5,6-tetrahydro)-pyridyl group can be produced, for example, by the usual reaction of a compound of the formula $R_2'$—Ph—Mg-Hal, wherein Hal is halogen, e.g. bromine or chlorine, and $R_2'$ represents an optionally usaturated, aliphatic hydrocarbon radical other than ethynyl, with an N-lower alkyl-4-piperidone, and splitting-off of water from the resulting N-lower-alkylated 4-p-$R_2$-phenyl-4-hydroxy-piperidine in the usual manner, e.g. by means of a proton donor acid, e.g. with p-toluenesulphonic acid in benzene, toluene or a xylene.

Compounds of the formula (IV) wherein $R_1'$ represents an optionally N-lower-alkylated 4-(1,2,5,6-tetrahydro)-pyridyl group can be obtained also by the usual reaction of a compound of the formula $R_2$—Ph—CH(CH$_3$)=CH$_2$ with formaldehyde, e.g. in oligomeric form, e.g. as paraformaldehyde, or as an aqueous solution, i.e. with Formalin, and ammonia or a mono-lower-alkylamine or a salt thereof, in the presence of a proton donor acid, e.g. a hydrohalic acid, such as hydrochloric acid.

Compounds of the formula (IV) wherein $R_2'$ represents lower-alkenyl or lower alkynyl can be produced for example by converting in a corresponding compound of the formula lower-alkanoyl—Ph—$R_1'$ the lower alkanoyl group into lower alkynyl, for example by reaction with a phosphorus alkylide, such as a compound of the formula (phenyl)$_3$—P=lower alkylidene, or by reduction with sodium borohydride to the corresponding α-hydroxy-lower-alkyl group and acid-catalysed dehydration thereof to lower alkenyl, or, e.g., by chlorination with phosphorus pentachloride to the corresponding α,α-dichloro-lower-alkyl group and subsequent treatment with a strong base, such as sodium hydroxide solution or sodium methanolate. The said lower alkanoyl compounds can be obtained, e.g., by reaction of a compound of the formula $R_1'$—Ph—H with a lower-alkanoyl halide in the presence of aluminium trichloride.

The new compounds can also be produced by replacing in a compound of the general formula V

$$R_1''\text{—Ph—}R_2'' \qquad (V)$$

wherein $R_1''$ represents a radical $R_1$ and/or $R_2''$ represents a radical $R_2$, provided that at least one of these radicals carries at least one radical $X_3$ replaceable by one or two hydrogen atoms(s), or in a salt thereof, the radical or radicals $X_3$ by hydrogen; and, optionally, performing one or more of the aforementioned additional operations.

Groups $X_3$ replaceable by a hydrogen atom are for example carboxyl groups, sulphonyl groups derived from organic sulphonic acids, or in particular optionally etherified or especially esterified hydroxyl groups, or optionally etherified mercapto groups, particularly groups of the type mentioned which are bound to a benzylic carbon atom. Etherified hydroxyl groups are for example lower alkoxy groups, such as methoxy or ethoxy. Esterified hydroxyl groups are for example hydroxyl groups esterified with a mineral acid or organic carboxylic acid or sulphonic acid. Organic carboxylic acids are, e.g., optionally substituted benzoic acids or alkanecarboxylic acids, especially lower alkanecarboxylic acids, e.g. benzoic acid or acetic acid. Organic sulphonic acid are, e.g., benzene-, p-toluene-, p-bromobenzene-, methane-, ethane- or ethenesulphonic acid. Mineral acids are preferably hydrohalic acids, e.g. hydrochloric, hydrobromic or hydriodic acid. Etherified mercapto groups are for example lower-alkylated or lower-alkenylated mercapto groups, such as methylthio, ethylthio or ethylenethio.

Groups $X_3$ replaceable by two hydrogen atoms are for example oxo or thiono groups, semicarbazono groups, or hydrazono groups optionally substituted in the $\beta$-position by organic sulphonyl, such as benzene-, p-toluene-, p-bromobenzene- or methanesulphonyl.

One and the same carbon atom can carry several such groups $X_3$ replaceable by hydrogen, e.g. two groups each replaceable by one hydrogen atom, such as hydroxyl, halogen or etherified mercapto groups, e.g. ethylenedithio, or one group replaceable by two hydrogen atoms, as well as one group replaceable by one hydrogen atom, such as an oxo group and an optionally esterified or etherified hydroxyl group.

The replacement with hydrogen can be performed in the customary manner; in the case of optionally esterified or etherified hydroxyl or mercapto groups, sulphonyl groups and radicals $X_3$ replaceable by two hydrogen atoms for example by reduction. Carboxyl can be replaced by a hydrogen atom for example by customary decarboxylation, such as by thermal decarboxylation.

Suitable reducing agents are in particular: nascent hydrogen generated for example by reaction of a compound containing unstable hydrogen with metals, e.g. with a proton-donor acid, such as a hydrohalic acid or lower alkanecarboxylic acid, with iron or optionally amalgamated zinc, magnesium or aluminium, or by reaction of water with, preferably amalgamated, aluminium, magnesium or sodium, e.g. with sodium amalgam; or e.g. hydrogen catalytically activated by a hydrogenation catalyst, such as a nickel or nobel metal catalyst, e.g. by Raney nickel or by platinum or palladium, optionally in chemically bound form, e.g. as oxide, or bound to a carrier, such as by palladium on charcoal or by platinum oxide; also low-valent transition metal compounds, such as tin-II or chromium-II salts, e.g. tin-II chloride, or hydrides such as calcium hydride or the boron hydride/tetrahydrofuran complex, or di-light-metal hydrides, such as sodium- or lithiumaluminium hydride, sodium-bis-(2-methoxyethoxy)-aluminium hydride or sodium-tris-(2-dimethylaminoethoxy)-aluminium hydride, sodium borohydride or sodium cyanoborohydride.

The reduction can be performed in the usual manner by reaction with one of the mentioned reducing agents known in the respective case from the literature as being suitable.

Optionally esterified or etherified hydroxyl groups bound to a benzylic carbon atom, as well as ketonic and aldehydic oxo groups, can be reductively replaced by hydrogen in particular by customary reaction with, for example, as stated in the foregoing, catalytically activated hydrogen, for example with hydrogen in the presence of palladium on charcoal, if necessary in an inert solvent, such as a lower alkanol, a lower alkanoic acid or an aliphatic ether, e.g. in ethanol, acetic acid or dioxane, and/or under elevated pressure and/or at elevated temperature. It is also possible in an analogous manner to reduce carboxyl groups, especially non-benzylic carboxyl groups, to methyl groups.

Ketonic oxo groups, sulphonyl groups and etherified mercapto groups can also be reduced by the usual reaction with nascent hydrogen, generated for example as described in the foregoing, for example using the Clemmensen method, preferably with zinc and hydrochloric acid.

Halogen, as well as lactamic or amidic oxo groups, can be replaced by hydrogen also by customary reaction with a suitable di-light-metal hydride, such as with one of those mentioned, if necessary in an inert solvent and/or at elevated temperature, e.g. at boiling temperature, starting with halogen compounds, for example with sodium borohydride in water, alcohols such as ethanol, glycol ethers such as ethylene glycol monomethyl ether, or amines such as triethylamine, with sodium-bis-(2-methoxyethoxy)-aluminium hydride in aromatic or araliphatic hydrocarbons such as benzene or toluene, or with sodium tris-(dimethylaminoethoxy)-aluminium hydride, or starting with lactams, for example with lithium aluminium hydride in an aliphatic ether, e.g. in diethyl ether, tetrahydrofuran or dioxane, if necessary at boiling temperature.

Hydrazono groups substituted as given, e.g. $\beta$-(p-toluenesulphonyl)-hydrazono, can be replaced by hydrogen in particular by the usual reaction with a di-light-metal hydride, e.g. with sodium cyanoborohydride in hexamethylphosphoric acid triamide, if necessary at elevated temperature. Semicarbazono groups or unsubstituted hydrazono groups can be replaced by hydrogen in particular by customary reaction with a strong base, for example by the Wolff-Kishner method, with an alkali alcoholate, e.g. with sodium methylate, if necessary under elevated pressure and/or at elevated temperature, or by the Huang-Minlon modification with an alkali metal hydroxide, e.g. potassium hydroxide, in an inert, high-boiling solvent, e.g. in di- or triethylene glycol or diethylene glycol monomethyl ether.

In a preferred embodiment of the preceding process, a compound of the general formula (V), wherein $R_1''$ represents a radical $R_1$ substituted in the 4-position by a hydroxyl group optionally etherified or esterified as given, and/or $R_2'$ represents a radical $R_2$ substituted by a hydroxyl group optionally etherified or esterified as given, by oxo and/or, on a terminal carbon atom, by oxo and optionally etherified hydroxyl, e.g. lower alkoxy, is reacted, e.g. as described, with catalytically activated hydrogen, for example hydrogen in the presence of palladium on charcoal, for example in acetic acid as an inert solvent, and if necessary under elevated pressure and/or at elevated temperature.

In another preferred embodiment of the preceding process, the starting material is for example a compound of the general formula V in which $R_1''$ represents a radical of the formula

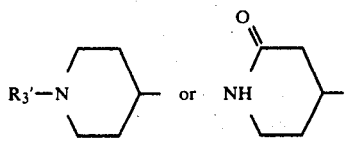

wherein $R_3'$ represents an esterified carboxyl group, e.g. carbomethoxy or carboethoxy, or an oxoalkyl radical derived from a lower alkyl group $R_3$, e.g. an α-oxoalkyl radical, and the oxo group and/or the esterified carboxyl group or the oxoalkyl group $R_3'$ is reduced by a customary reaction with a stated di-light-metal hydride, e.g. with lithium aluminium hydride, in an inert solvent, e.g. in diethyl ether or tetrahydrofuran, if necessary at boiling heat.

A further preferred embodiment comprises subjecting for example a compound of the formula V in which $R_1''$ represents a radical

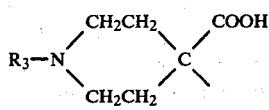

to, for example, thermal decarboxylation.

The starting materials of the formula (V) are known or they can be produced by methods known per se.

Compounds of the formula (V) wherein $R_1''$ represents an N-lower-alkylated $R_1$ substituted in the 4-position by hydroxyl can be obtained, for example, by a customary reaction of a 1-lower-alkyl-4-piperidone with a compound of the formula $R_2$—Ph—MgCl, —MgBr or —MgI in an inert solvent, e.g. in diethyl ether or tetrahydrofuran. There can then be obtained from for example the 4-hydroxyl compounds of the formula (V) thus obtained, by reaction with an esterifying agent, such as with a carboxylic acid halide or sulphonic acid halide or with a halogenating agent, e.g. with thionyl chloride or phosphorus tribromide, the corresponding compounds of the formula (V) wherein $X_4$ represents an esterified hydroxyl group.

Compounds of the formula (V) wherein $X_3$ represents carboxyl or sulphonyl can be obtained, for example, by reaction of a corresponding phenylacetic acid ester or benzylsulphone with an N,N-bis-(2-halogenoethyl)-lower-alkylamine in the customary manner, and optionally hydrolysis of the ester obtained.

Compounds of the formula (V) wherein $R_1''$ represents a 4-(2-oxo)-piperidyl radical can be obtained, for example, by the usual cyclisation of an optionally N-lower-alkylated δ-amino-2-(p-$R_2$-phenyl)-valeric acid.

Compounds of the formula (V) wherein $R_2'$ represents a radical $R_2$ substituted in the α-position by oxo can be obtained, for example, by a customary reaction of a compound of the formula $R_1$—Ph—H with a carboxylic acid derived from a compound of the formula $R_2$—H, or with the anhydride or chloride thereof, for example according to Friedel-Crafts in the presence of a Lewis acid, e.g. aluminium chloride, in an inert solvent, e.g. in dichloroethane or carbon disulphide. There can then be obtained from these, by a customary reaction with a hydrazine, optionally substituted as given, the corresponding hydrazono compounds, or by reaction with a sulphurising agent, e.g. with phosphorus pentasulphide or aluminium trisulphide, the corresponding thiono compounds.

Compounds of the formula (V) wherein $R_2'$ represents a radical $R_2$ substituted in the α-position by oxo or hydroxyl can however be produced also by a customary reaction of an N-lower-alkylated compound of the formula $R_1$—Ph—M in which M represents an alkali metal, e.g. lithium, or a group —MgCl, —MgBr or —MgI, with an acid halide, aldehyde or ketone derived from a compound of the formula $R_2$—H, preferably in an inert solvent, e.g. in diethyl ether or tetrahydrofuran, in the case of reaction with acid chloride advantageously at a greatly reduced temperature and/or with the addition of a cadmium halide, e.g. cadmium bromide. The hydroxyl compounds can however also be obtained from the corresponding oxo compounds by a customary reduction of the oxo group, e.g. with lithium aluminium hydride. There can then be obtained from the hydroxyl compounds, by reaction with etherifying or esterifying agents, e.g. with diethyl sulphate, a carboxylic or sulphonic acid halide, or a halogenating agent such as thionyl chloride or phosphorus tribromide, the corresponding compounds in which $R_2'$ contains an etherified or esterified hydroxyl group. The corresponding carboxylic acids of the formula (V) can subsequently be obtained from the halogen compounds, for example thus obtained, by customary reaction with sodium cyanide or potassium cyanide, and hydrolysis of the nitrile obtained, or by reaction with magnesium and then with carbon dioxide.

Compounds of the formula (V) wherein $R_2'$ represents a radical $R_2$ substituted by carboxyl can however also be obtained by reaction of a compound of the formula (V), obtained for example by one of the preceding formation processes, wherein $R_2'$ contains oxo, with an α-halogenoalkanoic acid ester and zinc, whereby, depending on the reaction conditions, α,β-unsaturated esters or β-hydroxyl esters are obtained; or by aldol condensation with a lower alkanoic acid, e.g. with acetic acid or an ester thereof, for example by the Perkin method, whereby α,β-unsaturated acids or esters are obtained. Esters optionally obtained can then be hydrolysed to the acids in the usual manner.

The new compounds can also be produced by reacting a mixture of compounds of the general formulae VI and VII

and

wherein one of the radicals $R_o$ and $R_o'$ represent an N-loweralkylated radical $R_1$, and the other represents a radical $R_2$, and $X_4$ represents an optionally reactive esterified hydroxyl group, or a bond extending to an adjacent carbon atom, with a suitable acid agent, and optionally performing one or more of the additional operations mentioned.

The radical $X_4$ is, in particular, reactive esterified hydroxyl, especially halogen having atomic number 17 and higher, such as chlorine.

Suitable acid agents are for example mineral acids, such as hydrofluoric acid, or oxyacids of phosphorus or sulphur, optionally in anhydride form, e.g. phosphoric acid, diphosphoric acid, polyphosphoric acids or phosphorus pentoxide or sulphuric acid, or in particular Lewis acids, such as halides of elements of the main groups III, IV and V and of the subgroups II and VIII of the periodic system of the elements, such as of boron, aluminium, gallium, tin, antimony and iron, e.g. besides iron trichloride, zinc chloride, tin chloride and antimony pentachloride, especially boron trichloride and boron trifluoride and aluminium trichloride and aluminium tribromide, also complex metallic acids, such as tetrafluoroboro- or hexachloroantimonic acid.

The reaction is performed in the customary manner, for example in an inert solvent, such as carbon disulphide, nitrobenzene, tetrachloromethane, diethyl ether, tetrahydrofuran or in an excess of the starting material of the formula (VII), at normal or moderately elevated or lowered temperature, e.g. at about $-30°$ to about $+100°$ C., advantageously with the exclusion of moisture and/or under a protective gas, e.g. under nitrogen.

In a preferred embodiment of the present process, there is reacted for example a mixture of compounds of the formulae (VI) and (VII), wherein $R_o$ represents a 1-lower-alkylpiperidyl radical, $R_o'$ represents lower alkyl, and $X_4$ represents chlorine or bromine, with aluminium trichloride, with the reaction preferably being performed in boiling carbon disulphide.

The starting materials of the formula (VI) are known, or can be obtained in a manner known per se.

Compounds of the formula (VI) wherein $R_o$ represents an N-lower-alkylpiperidyl radical can be produced for example by reacting a corresponding N-lower-alkyl-4-piperidone with an optionally substituted phenylmagnesium bromide; and partially hydrogenating the 1-lower-alkyl-4-hydroxy-4-phenyl-piperidine compound thus obtainable, if necessary after previously splitting off water, in the usual manner, e.g. in the presence of palladium charcoal.

The new compounds can also be produced by reacting together compounds of the general formulae VIII and IX

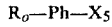  (VIII)

and

  (IX)

wherein one of the radicals $R_o$ and $R_o'$ represents an N-lower-alkylated radical $R_1$, and the other represents a radical $R_2$, and one of the radicals $X_5$ and $X_6$ represents an alkali metal atom or a group —MgHal, and the other represents a halogen atom Hal; and, optionally, performing one or more of the aforementioned additional operations.

An alkali metal atom is, e.g., lithium. A suitable halogen atom is for example chlorine, bromine or iodine.

The reaction can be performed in the customary manner, for example in an inert solvent, such as an aliphatic ether, e.g. in diethyl ether, tetrahydrofuran or dioxane, or starting with lithium compounds (VIII) and (IX) in a hydrocarbon, such as hexane or benzene, if necessary in the presence of a catalytic agent, such as a transition metal salt, e.g. a halide, such as chloride, of copper, and/or at elevated temperature, e.g. at boiling temperature.

The starting materials of the general formula (VIII) and (IX) are known, or they can be produced by methods known per se.

Those components in which $X_5$ or $X_6$ represents an alkali metal or a group —MgHal are preferably produced in situ, for example by a customary reaction of the corresponding halogen compound with an alkali metal, e.g. lithium, or with magnesium, advantageously in a finely dispersed form in an inert solvent, such as an aliphatic ether, e.g. in one of those mentioned, and used advantageously without isolation. The halogen compounds used for the purpose and for the reaction according to the invention can be obtained, for example, by customary halogenation, e.g. with bromine or chlorine, or with N-chlorosuccinimide, of a compound of the formula $R_o$—Ph—H, or by reduction of the oxo group, in a 1-lower-alkyl-4-oxo-piperidine, to the hydroxyl group, and subsequent reaction with a halogenating agent, e.g. with thionyl chloride or phosphorus tribromide, in the usual manner.

In the practical carrying out of the production processes described in the foregoing, it can be advantageous to combine several of the given methods.

Thus, for example, in an unsaturated radical, corresponding to the radical $R_1$ and substituted on the nitrogen atom by a radical $X_2$ which can be split off by solvolysis or by reduction, the solvolytic or reductive splitting-off of the radical $X_2$ can be performed simultaneously with the reduction of the double bond(s) by starting, for example, either with an N-acyl-1,2,5,6-tetrahydropyridine derivative, e.g. an N-acetyl-1,2,5,6-tetrahydropyridine derivative, or with an N-benzyl- or N-carbobenzoxy-1,2,5,6-tetrahydropyridyl compound. It is possible in an analogous manner also to perform the reductive exchange of a radical $X_3$ for hydrogen simultaneously with the solvolytic or reductive splitting-off of a radical $X_2$ and/or with the reduction of the double bond(s) in the azacycloalkenyl moiety.

There are advantageously used for performing the reactions according to the invention those starting materials which lead to the groups of final materials particularly mentioned at the beginning of the text, and especially to the final materials specifically described or emphasised.

In compounds of the general formula (I), obtainable for example in the given manner, it is possible within the limits of the definition of the final materials to introduce, convert or split off substituents.

Thus in compounds of the formula (I) wherein $R_3$ represents hydrogen it is possible to introduce lower alkyl $R_3$ in the customary manner, for example by the usual reaction with an alkylating agent, such as with a reactive ester, preferably a halogen ester or sulphonic acid ester, e.g. the hydrochloric, hydrobromic or hydriodic acid ester or benzene-, p-toluene-, p-bromobenzene- or methanesulphonic acid ester, of a lower alkanol, or, under reducing conditions, with a lower alkanol or di-lower-alkyl ketone, for example in the presence of hydrogen catalytically activated, e.g., by palladium, platinum or compounds thereof, such as palladium on charcoal or Raney nickel, if necessary in an inert solvent and/or under elevated pressure and/or at elevated temperature.

Furthermore, it is possible in compounds of the formula (I) in which the radical Ph contains at least one hydrogen atom which can be substituted to introduce one or more of the substituents mentioned, particularly halogen or nitro. The phenyl substitution can be performed in the usual manner; for the introduction of halogen for example by reaction with a customary nucleus-halogenating agent, e.g. with bromine in the presence of iron, or with N-chlorosuccinimide or the complex thereof with dimethylformamide, if necessary in an inert solvent; and for the introduction of nitro by customary nitration, e.g. by means of fuming nitric acid.

The introduction of lower alkoxy or halogen can also be effected however by firstly nitrating in the usual manner the compound to be substituted, e.g. by means of a nitric acid/sulphuric acid mixture; reducing in the resulting nitro compound in the customary manner, e.g. with catalytically activated hydrogen, the nitro group to the amino group; diazotising this in the usual manner, e.g. with nitrous acid; and reacting the resulting diazonium salt in the customary manner with a Cu-I-halide, e.g. according to Sandmeyer, or boiling it down with a lower alkanol; with the corresponding compound of the formula (I) substituted by halogen or by lower alkoxy being obtained.

It is also possible in compounds of the formula (I) to split off substituents of Ph, especially halogen. The splitting-off of substituents can be effected in the usual manner. Halogen can be split off for example reductively, e.g. by reaction with hydrogen in the presence of a hydrogenating catalyst, such as one of those mentioned, e.g. palladium on charcoal or Raney nickel, if necessary in an inert solvent and/or under elevated pressure and/or at elevated temperature, or with a suitable di-light-metal hydride, e.g. with sodium bis-(2-methoxyethyl)-aluminium hydride, in an inert solvent, e.g. in benzene or toluene, if necessary at elevated temperature.

Moreover, from compounds of the formula (I) wherein $R_3$ represents lower alkyl, particularly methyl, this group can be exchanged for hydrogen in the customary manner, for example by reaction with a halogenoformic acid ester, e.g. with ethyl chloroformate, advantageously in excess and, if necessary, in an inert solvent, e.g. in chloroform or benzene, and/or at elevated temperature, e.g. at boiling temperature; and by subsequent normal hydrolysis of the resulting carbamate, for example in the presence of an acid, e.g. a hydrohalic acid such as hydrochloric acid, or of a base, e.g. an alkali metal hydroxide.

The reactions mentioned are performed in the usual manner in the presence or absence of diluents, condensation agents and/or catalytic agents, at reduced, normal or elevated temperature, and optionally in a closed vessel.

Depending on the process conditions and starting materials, the compounds of the general formula (I) are obtained in the free form or in the form, likewise embraced by the invention, of their salts, preferably their acid addition salts. It is thus possible to obtain basic, neutral or mixed salts, and optionally also hemi-, mono-, sesqui- or polyhydrates thereof. The acid addition salts of the new compounds can be converted in a manner known per se into the free compound, e.g. with basic agents, such as alkalies or ion exchangers. Alternatively, the free bases obtained can form salts with organic or inorganic acids. For producing acid addition salts, there are used in particular those acids which are suitable for forming therapeutically applicable salts. The following may be mentioned as examples of such acids: hydrohalic acids, sulphuric acid, phosphoric acid, nitric acid, perchloric acid, aliphatic, alicyclic, aromatic or heterocyclic carboxylic or sulphonic acids, such as formic, acetic, propionic, succinic, glycolic, lactic, malic, tartaric, citric, ascorbic, maleic, hydroxymaleic, pyruvic, phenylacetic, benzoic, p-aminobenzoic, anthranilic, p-hydroxybenzoic, salicylic, p-aminosalicyclic, embonic, methanesulphonic, ethanesulphonic, hydroxyethanesulphonic, ethylenesulphonic, halogenobenzenesulphonic, toluenesulphonic, naphthalenesulphonic or sulphanilic acid.

These or other salts of the new compounds, such as the picrates, can also be used for purification of the free bases obtained, e.g. by a process wherein the free bases are converted into salts, these are separated and the free bases are again liberated from the salts. By virtue of the close relationship between the new compounds in the free form and in the form of their salts, it is to be taken, in the foregoing and in the following, that by the term 'free compounds' is meant, where the case applies and with the appropriate modifications, also the corresponding salts.

The invention relates also to those modifications of a process whereby a process is interrupted at some stage, or whereby a compound occurring as an intermediate at some stage is used as the starting material and the uncompleted steps are performed, or whereby a starting material is used in the form of a salt and/or racemate or antipode, or in particular is formed under the reaction conditions.

Depending on the choice of starting materials and operating procedures, the new compounds can be in the form of one of the various stereoisomers or in the form of a mixture of stereoisomers, e.g. depending on the number of asymmetric carbon atoms, in the form of pure optical isomers, e.g. in the form of a pure antipode, or in the form of isomeric mixtures, such as racemates, mixtures of diastereoisomers or mixtures of racemates.

Resulting diastereomeric mixtures and racemate mixtures can, by virtue of the physical-chemical differences in the constituents, be separated in a known manner into the pure diastereoisomers or racemates, for example by chromatography and/or fractional crystallisation.

Racemates obtained can be resolved by known methods, for example by recrystallisation from an optically active solvent, with the aid of microorganisms, or by reaction of a basic final material with an optically active acid forming salts with the racemic base, and separation of the salts obtained in this manner, e.g. by virtue of their different degrees of solubility, into the diastereoisomers from which the antipodes can be liberated by the action of suitable agents. Particularly suitable optically active acids are, for example, the D- and L-forms of tartaric acid, di-o-toluyltartaric acid, malic acid, mandelic acid, camphorsulphonic acid or quinic acid. It is advantageous to isolate the more effective of the two antipodes.

The pharmacologically applicable compounds of the present invention can be used, e.g., for producing pharmaceutical preparations containing an effective amount of the active substance together or in admixture with inorganic or organic, solid or liquid, pharmaceutically applicable carrier substances suitable for enteral administration. There are preferably used tablets or gelatine capsules which contain the active substance together with diluents, e.g. lactose, dextrose, sucrose, mannitol, sorbitol, cellulose and/or glycerin; and lubricants, e.g. diatomaceous earth, talcum, stearic acid or salts thereof, such as magnesium stearate or calcium stearate, and/or polyethylene glycol; tablets also contain binders, e.g. magnesium silicate, starches such as maize starch, wheat starch, rice starch or arrowroot starch, gelatine, tragacanth, methylcellulose, sodium carboxymethylcellulose and/or polyvinylpyrrolidone, and, if desired, effervescent agents, e.g. starches, agar, alginic acid or a salt thereof, such as sodium alginate, enzymes of binders and/or effervescent mixtures, or adsorbents, dyestuffs, flavourings and sweetening agents. Preparations which can be administered in the form of injections are preferably isotonic aqueous solutions or suspensions; suppositories or ointments, particlly fat emulsions or fat suspensions. The pharmacological preparations can be sterilised and/or can contain auxiliaries, e.g. preservatives, stabilisers, wetting and/or emulsifying agents, solubility-promoting agents, salts for regulation of the osmotic pressure, and/or buffer substances. The present pharmaceutical preparations, which, if desired, can contain further pharmacologically valuable substances, are produced in a manner known per se, e.g. by means of conventional mixing, granulating or coating processes; and they contain from about 0.1% to about 75%, especially from about 1% to about 50%, of active substance.

The compounds according to the invention are administered to a warm-blooded animal about 75 kg in weight advantageously in daily doses of about 5 to about 150 mg, e.g. from about 10 to about 75 mg, preferably in the form of several equal doses spread over the day.

The invention is described in more detail in the Examples which follow. The temperature values are given in degrees Centigrade.

EXAMPLE 1

1.2 g of palladium (5% on charcoal) is added to a solution of 12.0 g of α-[p-(4-piperidyl)-phenyl]-ethanol in 120 ml of glacial acetic acid, and the solution is hydrogenated at 40°–50° at normal pressure until 1 equivalent of hydrogen has been absorbed. The catalyst is then filtered off and the filtrate is concentrated in vacuo to dryness. The crude 4-(4-ethylphenyl)-piperidine remaining behind in the residue is further purified by treatment with active charcoal and subsequent conversion into the hydrochloride. The melting point of the hydrochloride is 198°–202° (from ethanol/ether).

EXAMPLE 2

The necessary amount of a warm 10% solution of L-tartaric acid in ethanol is added to 5 g of 4-(4-ethylphenyl)-piperidine in the smallest possible amount of ethanol. After cooling, and if necessary after the addition of ether, 4-(4-ethylphenyl)-piperidine-L-tartrate, m.p. 166°–167° (from ethanol), crystallises out.

In an analogous manner can be obtained the fumarate, m.p. 196°–197° (from ethanol) and also the methanesulphonate, m.p. 147°–148° (from ethanol/ether).

EXAMPLE 3

To a solution of 15 g of N-acetyl-4-(2-chloro-4-acetyl-phenyl)-piperidine in 60 ml of ethylene glycol and 10 ml of hydrazine hydrate is added 10 g of finely powdered sodium hydroxide, and refluxing is performed for 2 hours. In the course of the next 4 hours, the temperature of the heating bath is slowly raised to 220° C., with the unreacted hydrazine as well as the water formed during the reaction being distilled off. After expiration of this time, the temperature inside the reaction vessel is 195°. The reaction mixture is cooled to room temperature; 100 ml of water is added, and extraction is performed three times with 100 ml of ether each time. The organic phases are dried over sodium sulphate and concentrated in vacuo. The residue is distilled under high vacuum, and in the fraction boiling at b.p.$_{0.05}$ = 130° oily 4-(2-chloro-4-ethyl-phenyl)-piperidine passes over. The hydrochloride melts at 245°–246°.

The N-acetyl-4-(2-chloro-4-acetyl-phenyl)-piperidine used as starting material can be produced for example as follows:

3 g of N-acetyl-4-(4-acetyl-phenyl)-piperidine is added at −15°, with stirring, to 20 ml of fuming nitric acid, and the reaction mixture is subsequently stirred for 30 minutes at a temperature of between 0° and 15°. It is then poured onto 100 g of ice; the pH value is adjusted to 14 with concentrated sodium hydroxide solution, and extraction is performed three times with 50 ml of methylene chloride each time. The organic phases are combined, washed until neutral, dried over sodium sulphate and concentrated in vacuo. The residue is dissolved in ether/ethanol and treated with active charcoal. The crude oily N-acetyl-4-(2-nitro-4-acetyl-phenyl)-piperidine, obtained after filtration and concentration by evaporation, can be further reacted without additional purification.

A solution of 23 g of crude N-acetyl-4-(2-nitro-4-acetylphenyl)-piperidine in 250 ml of ethanol is hydrogenated with 4.5 g of palladium (5%) on barium carbonate (decomposed) until 3 equivalents of hydrogen have been absorbed. The catalyst is then filtered off, and the filtrate is concentrated in vacuo to dryness. The crude N-acetyl-4-(2-amino-4-acetyl-phenyl)-piperidine thus obtained is purified by way of the hydrochloride, m.p. 220°–222° (from ethanol).

A solution of 4.5 g of sodium nitrite in 10 ml of water is added dropwise at 0°, with stirring, to a suspension of 16 g of N-acetyl-4-(2-amino-4-acetyl-phenyl)-piperidine in 75 ml of concentrated hydrochloric acid and 75 ml of water; stirring is continued at 0° for 2 hours; the reaction solution, which is now clear, is transferred to a dropping funnel precooled to 0°, and is slowly added dropwise to a solution, cooled to 0° and being stirred, of 16 g of copper-I-chloride in 150 ml of semi-concentrated hydrochloric acid. Stirring is maintained at 15° until the evolution of nitrogen has ceased (about 1 hour). An addition of 300 ml of water is made, and extraction is performed three times with 150 ml of ethyl acetate each time. The organic phases are extracted three times at 0° with 150 ml of 2 N sodium hydroxide solution each time; they are then cleared by filtration, washed neutral, dried over sodium sulphate and concentrated in vacuo. The oily N-acetyl-4-(2-chloro-4-acetyl-phenyl)-piperidine obtained in this manner can be used without purification.

EXAMPLE 4

4-(4-Isobutyl-phenyl)-piperidine hydrochloride (m.p. 258°–262° (from ethanol/acetone) is obtained by catalytic hydrogenation, in a manner analogous to that described in Example 1, starting with 6 g of 1-[4-(4'-piperidyl)-phenyl]-isobutanol hydrochloride. The production of the starting material is described in the Belgian Pat. No. 804,203.

EXAMPLE 5

4-(2,4-Dimethylphenyl)-piperidine hydrochloride (m.p. 283°–285° (from ethanol/ether) is obtained, in a manner analogous to that described in Example 1, starting with 13 g of N-benzyl-4-(2,4-dimethyl-phenyl)-1,2,5,6-tetrahydropyridine. The starting material can be obtained, by a process analogous to that described in Example 1, by conversion of 34 g of 4-bromo-m-xylene into the bromomagnesium compound, according to Grignard; reaction of this compound with 38 g of N-benzyl-4-piperidone; and splitting-off of water by means of acetic acid/hydrochloric acid. The product obtained boils at 0.05 mm Hg at about 170°.

EXAMPLE 6

0.5 g of palladium (5% on charcoal) is added to a solution of 2.5 g of N-benzyl-1,2,5,6-tetrahydro-4-(2-methoxy-4-acetylphenyl)-pyridine in 30 ml of acetic acid and 3 ml of concentrated hydrochloric acid, and the solution is hydrogenated under normal pressure until 3 equivalents of hydrogen have been absorbed. The catalyst is then removed by filtration, and the filtrate is concentrated in vacuo to dryness. The residue is fractionally distilled under high vacuum, and, in the fraction boiling at $b.p._{0.001}=130°$, crude oily 4-(2-methoxy-4-ethyl-phenyl)-piperidine passes over. The hydrochloride melts at 238°–239° (from ethanol/ether). The starting material can be produced in the following manner:

A solution of 14 g of 3-methoxy-4-bromoacetophenoneethylene ketal in 150 ml of absolute tetrahydrofuran is slowly added dropwise at 60°, with the exclusion of water, to a suspension of 1.3 g of magnesium chips in 10 ml of absolute tetrahydrofuran. As soon as all the magnesium has gone into solution, the temperature is lowered to 10°, and a solution of 9.5 g of N-benzyl-4-piperidone in 130 ml of absolute tetrahydrofuran is added dropwise. After completion of the addition, concentration in vacuo to dryness is performed, and the residue is triturated with anhydrous ethyl ether, and filtered off with suction. The suction-filter residue is subsequently distributed between three-times 200 ml of ether and 200 ml of saturated, cold, aqueous ammonium chloride solution. The organic phases are combined, washed until neutral, dried over sodium sulphate and concentrated in vacuo to dryness. The crude 3-methoxy-4-(N-benzyl-4-hydroxy-4-piperidyl)-acetophenoneethylene ketal obtained in this manner can be reacted without further purification. It is dissolved in 100 ml of acetic acid and 30 ml of concentrated hydrochloric acid, and the solution is refluxed for two hours. It is then concentrated in vacuo to dryness; the pH value is adjusted with 2 N sodium hydroxide solution to 14, and extraction is carried out 3 times with 50 ml of ether each time. The organic phases are combined, washed until neutral, dried over sodium sulphate and concentrated in vacuo. The residue is chromatographed on 300 g of silica gel, with ether as the eluant, to yield N-benzyl-1,2,5,6-tetrahydro-4-(3-methoxy-4-acetylphenyl)-piperidine in the form of a colourless oil, which can be used without further purification.

EXAMPLE 7

A solution of 14 g of N-carboethoxy-4-(4-ethyl-phenyl)-piperidine in 100 ml of absolute dioxane is slowly added dropwise at 80°–95°, in a nitrogen atmosphere, to a stirred suspension of 4 g of lithium aluminium hydride in 300 ml of absolute dioxane. After completion of the addition, refluxing is performed for 3 hours. The reaction mixture is then cooled to 10°, and 120 ml of water is added dropwise. The resulting precipitate is filtered off with the aid of kieselguhr, and concentrated in vacuo. To the residue is added 100 ml of ether, and filtration is performed using kieselguhr. The filtrate is concentrated to dryness, and the residue is treated with ethanolic hydrochloric acid to obtain N-methyl-4-(4-ethyl-phenyl)-piperidine hydrochloride, m.p. 209°–210°.

The starting material can be produced in the following manner:

A solution of 8.95 g of ethyl chloroformate in 80 ml of ether is added dropwise at 15°–20° in an inert atmosphere, with stirring, to a solution of 12 g of 4-(4-ethyl-phenyl)-piperidine in 8.4 g of triethylamine and 400 ml of ether. After completion of the addition, stirring is maintained for 2 hours at room temperature, and extraction with 500 ml of water is carried out. The organic phase is washed neutral, dried over sodium sulphate and concentrated in vacuo. From the evaporation residue is obtained, after extraction with petroleum ether in the cold state, N-carboethoxy-4-(4-ethyl-phenyl)-piperidine, m.p. 71°.

EXAMPLE 8

N-Ethyl-4-(4-ethyl-phenyl)-piperidine, $b.p._{0.01}=100°$, is obtained by catalytic hydrogenation, in a manner analogous to that described in Example 1, starting with 12 g of p-(N-ethyl-4-piperidyl)-acetophenone. The hydrochloride melts at 119°–120° (from ethanol/ether).

EXAMPLE 9

4-(4-Methyl-phenyl)-piperidine hydrochloride, m.p. 194°–195° (from ether/ethanol) is obtained by catalytic hydrogenation, in a manner analogous to that described in Example 6, starting with 17 g of N-benzyl-1,2,5,6-tetrahydro-4-(4-methylphenyl)-piperidine.

The starting material can be produced by conversion of p-bromotoluene with magnesium into the magnesium compound, reaction with N-benzyl-4-piperidone, and subsequent splitting-off of water. The product obtained melts at 40°–41° (from cold pentane).

EXAMPLE 10

4-(4-Methylphenyl)-piperidine hydrochloride, m.p. 194°–195° (from ether/ethanol) is obtained, in a manner analogous to that described in Example 1, starting with 17 g of 1,2,5,6-tetrahydro-4-(4-methylphenyl)-piperidine.

EXAMPLE 11

4-(4-Methylphenyl)-piperidine hydrochloride, m.p. 194°–195° (from ethanol/ether) is obtained by catalytic hydrogenation, in a manner analogous to that described in Example 10, starting with 16 g of 4-hydroxy-4-(4-methylphenyl)-piperidine.

The starting material can be produced in the following manner: In a manner analogous to that described in Example 6, 100 g of p-bromotoluene and 110 g of N-benzyl-4-piperidone are reacted to give N-benzyl-4-hydroxy-4-(4-methylphenyl)-piperidine, $b.p._{0.05}=185°$.

30 g of N-benzyl-4-hydroxy-4-(4-methylphenyl)-piperidine in a mixture of equal parts of ethyl acetate and ethanol with palladium (5% on charcoal) is hydrogenated until one equivalent of hydrogen has been absorbed to give 4-hydroxy-4-(4-methylphenyl)-piperidine, m.p. 137°–138° (from ethyl acetate).

EXAMPLE 12

11.4 g of N-acetyl-4-(4-n-propylphenyl)-piperidine in 100 ml of concentrated hydrochloric acid, if necessary with the addition of glacial acetic acid as a solubility-promoting agent, is refluxed for 2 hours. The reaction mixture is then highly concentrated in vacuo; it is adjusted with 10% sodium hydroxide solution to have a pH value of 14, and exhaustingly extracted with ether. The ether extracts are combined, treated with active charcoal and concentrated to dryness. The residue is distilled under high vacuum, and, in the fraction boiling at b.p.$_{0.05}$=130°–140°, 4-(4-n-propylphenyl)-piperidine passes over. The hydrochloride melts at 228°–230° (from ethanol/ether).

The starting material can be produced, for example, by reaction of 18 g of N-acetyl-4-phenyl-piperidine and 11.5 g of propionic acid chloride, in the presence of aluminium trichloride, to N-acetyl-4-(4-propionylphenyl)-piperidine and then catalytic hydrogenation thereof to give N-acetyl-4-(4-n-propylphenyl)-piperidine, b.p.$_{0.03}$=160°.

EXAMPLE 13

4-(4-n-butylphenyl)-piperidine, b.p.$_{0.04}$=120° (hydrochloride: m.p. 225°–230°, from ethanol/ether), is obtained, in a manner analogous to that described in Example 12, starting with 18 g of N-acetyl-4-phenyl-piperidine and 12.8 ml of butyric acid chloride, by way of N-acetyl-4-(4-butyrylphenyl)-piperidine and N-acetyl-4-(4-n-butylphenyl)-piperidine, b.p.$_{0.04}$=170°.

EXAMPLE 14

4-(3,5-Dinitro-4-ethylphenyl)-piperidine, m.p. 85°–86°, is obtained, in a manner analogous to that described in Example 12, starting with 1.1 g of N-acetyl-4-(3,5-dinitro-4-acetylphenyl)-piperidine.

The starting material can be produced for example as follows:

To 14 ml of fuming nitric acid is added portionwise at −15° to −10°, with stirring, 2 g of N-acetyl-4-(4-ethylphenyl)piperidine. The reaction mixture is subsequently stirred for two hours at −10° to 0°; it is then poured onto 100 g of ice, the pH value is brought to 14 with concentrated sodium hydroxide solution, and extraction is performed twice with 50 ml of methylene chloride each time. The organic phases are combined, washed until neutral, dried over sodium sulphate and concentrated in vacuo. There crystallises from the residue, after trituration with chloroform/ether, N-acetyl-4-(3,5-dinitro-4-acetylphenyl)-piperidine, m.p. 130°–131°.

EXAMPLE 15

The following are obtained in a manner analogous to that described in the Examples 1 to 14, or by one of the methods discussed in the descriptive part of the text:
- 1-ethyl-4-(p-ethylphenyl)-piperidine (e.g. by reduction of 1-acetyl-4-(p-ethylphenyl)-piperidine);
- 4-(4-ethyl-2-methoxy-phenyl)-piperidine (e.g. by reduction of 4-(4-acetyl-2-methoxy-phenyl)-piperidine);
- 4-(p-isobutylphenyl)-piperidine (by reaction of 1-acetyl-4-phenyl-piperidine with isobutyryl chloride in the presence of aluminium trichloride, reduction of the resulting ketone with hydrogen and palladium, and hydrolytic splitting-off of the N-acetyl group);
- 4-(4-ethyl-3-chlorophenyl)- and 4-(3,4-dimethylphenyl)-piperidine (by reaction of 1-benzyl-4-piperidone with 4-ethyl-3-chloro- and 3,4-dimethylphenylmagnesium bromide, respectively, splitting-off of water from the substituted 4-hydroxy-4-phenylpiperidine obtained, and subsequent reduction); and
- 1-ethyl-4-(p-isopropenylphenyl)-piperidine (by reaction of 1-ethyl-4-(p-acetylphenyl)-piperidine with triphenylmethylene-phosphorane).

EXAMPLE 16

0.6 g of 4-(4-ethylphenyl)-2-piperidone is added portionwise under nitrogen to a stirred suspension of 0.13 g of lithium aluminium hydride in 20 ml of absolute tetrahydrofuran. The mixture is subsequently stirred at 60° for one hour and is then cooled to room temperature; there are added dropwise 0.5 ml of water and then 0.1 ml of 2 N sodium hydroxide solution, and the whole is filtered through kieselguhr. The filtrate is concentrated by evaporation, and the resulting crude 4-(4-ethylphenyl)-piperidine is converted in the usual manner into the hydrochloride, which melts at 205°–208°.

The 4-(4-ethylphenyl)-2-piperidone used as starting material can be obtained, e.g., as follows:

A solution of 43 g of 4-ethylbenzaldehyde and 52 g of diethylphosphonoacetonitrile in 300 ml of methylene chloride is added dropwise within 15 minutes, with ice cooling, to a well-stirred emulsion of 6.5 g of tetrabutylammonium bromide in 180 ml of 50% sodium hydroxide solution and 150 ml of methylene chloride. Stirring is maintained at room temperature for 30 minutes, the organic phase is separated, washed neutral with water, dried over sodium sulphate and concentrated in vacuo. The crude p-ethyl-cinnamic acid nitrile thus obtained is added to a solution of 8 g of sodium in 53 g of malonic acid diethyl ester and 400 ml of absolute ethanol, and the mixture is refluxed for 2 hours. It is then concentrated in vacuo to a third of the volume; 500 ml of 0.5 N acetic acid is added, and extraction is performed three times with 500 ml of ether each time. The organic phases are washed until neutral, dried over sodium sulphate and concentrated in vacuo to dryness. Chromatography of the residue on 1 kg of silica gel with methylene chloride as the eluant yields 2-carboethoxy-3-(4-ethylphenyl)-4-cyano-butyric acid ethyl ester as colourless oil.

A solution of 31 g of the aforementioned compound in 1.6 g of triethylamine and 500 ml of absolute ethanol is hydrogenated with 8 g of Raney nickel until about 4 liters of hydrogen have been absorbed. The catalyst is removed by filtration, and the filtrate is concentrated in vacuo to dryness. 3-Carboethoxy-4-(4-ethylphenyl)-2-piperidone, m.p. 157°–159°, crystallises from the residue after trituration with ether.

A solution of 8 g of the aforemention compound in 110 ml of ethanol, 40 ml of 2 N sodium hydroxide solution and 50 ml of water is refluxed for 45 minutes. It is then concentrated in vacuo to dryness; the residue is acidified with 2 N hydrochloric acid to pH=1, and extracted with 500 ml of chloroform. The organic phase is washed neutral, dried over sodium sulphate and concentrated in vacuo. The crude crystalline 3-carboxy-4-(4-ethylphenyl)-2-piperidone, m.p. 125° (decomposition) remaining behind as residue is refluxed in 400 ml of toluene for 30 minutes. The reaction mixture is concentrated by evaporation to a volume of about 20 ml, and a small amount of ether is added, whereupon 4-(4-ethylphenyl)-2-piperidone, m.p. 165°, crystallises out.

EXAMPLE 17

5.0 g of crude 4-carboxy-4-(4-ethylphenyl)-1-methylpiperidine is heated in a flow of nitrogen for 30 minutes at about 250°. It is then cooled to about 100°, and distilled under high vacuum. The fraction boiling at 90° to 100° is further purified by chromatography on 50 g of silica gel with ethyl acetate and a small amount of methanol as the eluant. There is obtained 4-(4-ethylphenyl)-1-methyl-piperidine, which is converted in the usual manner into the hydrochloride, m.p. 209°-210°.

The starting material can be obtained as follows:

Starting with 4-ethylphenyl-acetonitrile, there is obtained with bis-(2-chloroethyl)-methylamine, by a process analogous to that described in U.S. Pat. No. 2,167,351, 4-carboethoxy-4-(4-ethylphenyl)-piperidine. Starting with 7 g of this crude ester, there is obtained, by treatment with 50 ml of 2 N sodium hydroxide solution in 100 ml of boiling ethanol, crude 4-carboxy-4-(4-ethylphenyl)-N-methyl-piperidone, which can be further processed without additional purification.

EXAMPLE 18

A solution of 6.7 g of 2-(4-ethylphenyl)-1,5-dibromopentane is added dropwise at 0°, with stirring, to a solution of 20 ml of 2 N sodium hydroxide solution and 0.64 g of methylamine in 100 ml of ethanol. After completion of the addition, the reaction mixture is heated in a bomb tube at 80° for 10 hours; it is then cooled to room temperature, decolorised with a small amount of sodium thiosulphate, concentrated in vacuo to dryness and distilled under high vacuum. The fraction boiling at 90°-120° (0.03 mm) is further purified by chromatography on silica gel with chloroform/methanol (15:1) as the eluant, and subsequently converted into the hydrochloride. 1-Methyl-(4-ethylphenyl)-piperidine hydrochloride melts at 209°-210°.

The 3-(4-ethylphenyl)-1,5-dibromopentane used as starting material can be produced, by a process analogous to that described in J. Amer. Chem. Soc.; 53, 1105 (1931), starting with the 2-carboethoxy-3-(4-ethylphenyl)-4-cyanobutyric acid ethyl ester described in Example 16, and boils at 175°-186° (12 mm Hg).

EXAMPLE 19

A few drops of methyl iodide are added, under nitrogen, to a suspension of 0.5 g of magnesium chips covered with a small amount of absolute ether and, after the reaction has subsided, there is added dropwise at 30° to 35° a solution of 4.2 g of 4-(4-chlorophenyl)-1-methyl-piperidine in 20 ml of absolute ether. When the major part of the magnesium has been dissolved, 100 mg of copper(I)iodide is added; the temperature is lowered to −10°, 2.5 g of ethyl bromide is added, and stirring is maintained over night at −10° to 0°. An addition of 50 ml of 2 N sodium hydroxide solution is then made, the mixture is saturated with sodium chloride, and extraction is performed three times with 50 ml of ether each time. The organic phases are combined, washed until neutral, dried over sodium sulphate and concentrated in vacuo. Distillation of the residue under high vacuum, and chromatography of the fraction boiling at 90°-100° (0.03 mm) on silica gel with chloroform and a small amount of methanol as the eluant yield crude 4-(4-ethylphenyl)-1-methyl-piperidine, which is converted into the hydrochloride, m.p. 209°-210°.

EXAMPLE 20

To a solution of 3.5 g of 1-methyl-4-phenyl-piperidine in 50 ml of tetrachloroethane are added, with stirring, 2.7 g of finely powdered aluminium chloride and subsequently 2.5 g of ethyl bromide, and the reaction mixture is stirred at 50° for 4 hours. An addition of 50 g of ice is made, the mixture is rendered alkaline (pH=14) with concentrated sodium hydroxide solution, and extracted three times with 100 ml of ethyl acetate each time. The organic phases are dried over sodium sulphate and concentrated in vacuo. After distillation of the residue under high vacuum, chromatographic purification of the fraction boiling at 85°-100° (0.04 mm), on silica gel with chloroform and a small amount of methanol as the eluant, yields crude 4-(4-ethylphenyl)-1-methyl-piperidine, which can be further purified by fractional crystallisation of the hydrochloride (m.p. 209°-210°).

The same compound can be produced in an analogous manner starting with 4-chloro-1-methyl-piperidine and ethyl benzene.

EXAMPLE 21

Tablets containing 100 mg of active substance, e.g. 4-(4-ethylphenyl)-piperidine, or the hydrochloride, tartrate, fumarate or methanesulphonate thereof, can be produced for example with the following composition:

| Composition | Per tablet |
|---|---|
| active substance, e.g. 4-(4-ethylphenyl)-piperidine | 100 mg |
| lactose | 50 mg |
| wheat starch | 73 mg |
| colloidal silicic acid | 13 mg |
| talcum | 12 mg |
| magnesium stearate | 2 mg |
| | 250 mg |

Production

The active substance is mixed with the lactose, a portion of the wheat starch and with colloidal silicic acid, and the mixture is put through a sieve. A further portion of wheat starch is made into a paste with the 5-fold amount of water on a water bath and the powder mixture is kneaded with this paste until a plastic mass is formed. This is pressed through a sieve having a mesh size of about 3 mm; it is dried and the dried granulate is again put through a sieve. The remainder of the wheat starch, the talcum and the magnesium stearate are then mixed in, and the mixture obtained is pressed into the form of tablets of 250 ml, which are provided with dividing groove(s).

We claim:

1. A compound of the formula I

wherein $R_1$ represents a radical of the formula

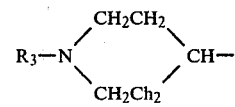

wherein $R_3$ represents hydrogen, Ph represents p-phenylene which is unsubstituted or is mono-substituted by lower alkyl having up to 4 carbon atoms, lower alkoxy having up to 4 carbon atoms or halogen up to atomic number 17, and $R_2$ represents lower alkyl having up to 4 carbon atoms, with the proviso, that $R_2$ contains at least 2 carbon atoms, when Ph is unsubstituted p-phenylene.

2. A compound as claimed in claim 1 being 4-(4-Ethylphenyl)-piperidine.

3. A compound as claimed in claim 1 being 4-(4-n-Butylphenyl)-piperidine.

4. A compound as claimed in claim 1 being 4-(4-Ethyl-2-methoxyphenyl)-piperidine.

5. A compound as claimed in claim 1 being 4-(4-n-Propylphenyl)-piperidine.

6. A compound as claimed in claim 1 being 4-(4-Isobutylphenyl)-piperidine.

7. A pharmaceutical preparation comprising an antidepressive effective amount of a compound according to claim 1 together with a pharmaceutically acceptable carrier.

* * * * *